US008496604B2

(12) United States Patent
Brohan et al.

(10) Patent No.: US 8,496,604 B2
(45) Date of Patent: Jul. 30, 2013

(54) SYSTEMS FOR AND METHODS OF ASSESSING URINARY FLOW RATE VIA SOUND ANALYSIS

(75) Inventors: John Brohan, Montreal (CA); Peter Zvara, Stowe, VT (US); Katarina Zvarova, Stowe, VT (US)

(73) Assignee: University of Vermont and State Agricultural College, Burlington, VT (US)

( * ) Notice: Subject to any disclaimer, the term of this patent is extended or adjusted under 35 U.S.C. 154(b) by 230 days.

(21) Appl. No.: 12/901,774

(22) Filed: Oct. 11, 2010

(65) Prior Publication Data

US 2011/0029603 A1    Feb. 3, 2011

Related U.S. Application Data

(62) Division of application No. 11/530,314, filed on Sep. 8, 2006, now Pat. No. 7,811,237.

(51) Int. Cl.
    *A61B 5/103* (2006.01)
    *A61B 5/117* (2006.01)
    *A61B 5/00* (2006.01)
    *B65D 81/00* (2006.01)
    *G01F 1/20* (2006.01)
    *G01F 1/66* (2006.01)

(52) U.S. Cl.
    USPC ............ 600/587; 73/861.18; 73/861.21; 600/573; 600/574

(58) Field of Classification Search
    USPC .......... 600/561, 573–574, 586; 702/103–104, 702/124, 126, 138–139
    See application file for complete search history.

(56) References Cited

U.S. PATENT DOCUMENTS

| 3,363,619 A | 1/1968 | Keitzer |
| 3,561,427 A | 2/1971 | Profy |

(Continued)

FOREIGN PATENT DOCUMENTS

| DE | 3541649 | 4/1987 |
| GB | 1219231 | 1/1971 |

(Continued)

OTHER PUBLICATIONS

"Assessment of an Electronic Daily Diary in Patients With Overactive Bladder," by P. Quinn, J. Goka and H. Richardson. Pfizer, Sandwich, Kent, UK. 2003 BJU International, 91, pp. 647-652.

(Continued)

*Primary Examiner* — Rene Towa
*Assistant Examiner* — Adam Eiseman
(74) *Attorney, Agent, or Firm* — Downs Rachlin Martin PLLC

(57) ABSTRACT

Systems for and methods of assessing urinary flow rate via sound analysis. Embodiments of the uroflow measurement systems include a computer and a telephone or a digital recording mechanism to capture the sound of one or more urination events, which are stored as audio files in a database. The uroflow measurement systems may include sound analysis software for analyzing the strength and duration of each urination event and may include a web-based uroflow software application for viewing the results via the Internet or other network. In one embodiment, the sound analysis software performs the steps of reading in the raw data of a selected audio file, generating a plot of the audio signal amplitude vs. time, generating a plot of smoothed data for the purpose of presenting an outline of the flow, generating a main flow plot, which is a plot of the largest continuous flow that has a strength that is greater than a predetermined minimum, and generating a set of numerical values that correspond to the strength and duration of urination.

8 Claims, 10 Drawing Sheets

U.S. PATENT DOCUMENTS

| | | | |
|---|---|---|---|
| 4,063,548 | A | 12/1977 | Klatt et al. |
| 4,099,412 | A | 7/1978 | Nehrbass |
| 4,343,316 | A | 8/1982 | Jespersen |
| 4,448,207 | A | 5/1984 | Parrish |
| 4,554,687 | A | 11/1985 | Carter et al. |
| 4,589,280 | A | 5/1986 | Carter |
| 4,658,834 | A | 4/1987 | Blankenship et al. |
| 4,683,748 | A | 8/1987 | Carter |
| 4,732,160 | A | 3/1988 | Ask et al. |
| 5,062,304 | A | 11/1991 | Van Buskirk et al. |
| 5,078,012 | A | 1/1992 | Ding et al. |
| 5,176,148 | A | 1/1993 | Wiest et al. |
| 5,331,548 | A | 7/1994 | Rollema et al. |
| 5,377,101 | A | 12/1994 | Rollema |
| 5,410,471 | A | 4/1995 | Alyfuku et al. |
| 5,495,854 | A | 3/1996 | Currie |
| 5,807,278 | A | 9/1998 | McRae |
| 5,823,972 | A | 10/1998 | McRae |
| 5,891,051 | A | 4/1999 | Han et al. |
| 6,506,169 | B2 | 1/2003 | Griffiths |
| 6,904,809 | B1 | 6/2005 | Aundal |
| 6,916,283 | B2 | 7/2005 | Tracey et al. |
| 6,931,943 | B1 | 8/2005 | Aundal |
| 7,194,369 | B2 | 3/2007 | Lundstedt et al. |
| 7,758,519 | B2 | 7/2010 | Brohan et al. |
| 2003/0097039 | A1 | 5/2003 | Besson et al. |
| 2004/0260163 | A1 | 12/2004 | Kron et al. |
| 2004/0260540 | A1 | 12/2004 | Zhang |
| 2006/0020225 | A1 | 1/2006 | Gerber et al. |
| 2008/0082022 | A1 | 4/2008 | Brohan et al. |
| 2008/0275366 | A1 | 11/2008 | Brohan et al. |

FOREIGN PATENT DOCUMENTS

| | | |
|---|---|---|
| WO | 2004084089 | 9/2004 |
| WO | 2007128539 | 11/2007 |
| WO | 2008030692 | 3/2008 |
| WO | 20090143113 | 11/2009 |

OTHER PUBLICATIONS

"A review of randomized controlled trials comparing the effectiveness of hand held computers with paper methods for data collection," by Shannon J. Lane, Nancy M. Heddle, Emmy Arnold and Irwin Walker. BMC Medical Informatics and Decision Making 2006, 6:23, 10 pages.

"The Voiding Audiograph: A New Voiding Test," by Walter A. Keitzer and Gene C. Huffman, The Journal of Urology, vol. 96, pp. 404-411, 1996.

"Urophonographic Studies of Benign Prostatic Hypertrophy," by Kenkicki Koiso, Ryosuke Nemoto and Mikinobu Ohtani, The Journal of Urology, vol. 145, pp. 1071-1077, May 1991.

Office Action dated Nov. 26, 2008 in related U.S. Appl. No. 11/530,314.

Response to Office Action dated Feb. 19, 2009 in related U.S. Appl. No. 11/530,314.

Office Action dated Apr. 2, 2009 in related U.S. Appl. No. 11/530,314.

Response to Office Action dated Jul. 2, 2009 in related U.S. Appl. No. 11/530,314.

Advisory Action dated Jul. 16, 2009 in related U.S. Appl. No. 11/530,314.

RCE dated Aug. 26, 2009 in related U.S. Appl. No. 11/530,314.

Office Action dated Sep. 11, 2009 in related U.S. Appl. No. 11/530,314.

Response to Office Action dated Dec. 11, 2009 in related U.S. Appl. No. 11/530,314.

Office Action dated Feb. 19, 2010 in related U.S. Appl. No. 11/530,314.

Response to Office Action dated May 19, 2010 in related U.S. Appl. No. 11/530,314.

Notice of Allowance dated Jun. 8, 2010 in related U.S. Appl. No. 11/530,314.

Related pending International Application No. PCT/US2007/076108 filed Aug. 16, 2007.

Related pending International Application No. PCT/US2009/044464 filed May 19, 2009.

Related pending U.S. Appl. No. 12/123,145, filed May 19, 2008.

International Search Report and Written Opinion dated Mar. 6, 2008 in related pending International Application No. PCT/US2007/076108 filed Aug. 16, 2007.

First Office Action dated Nov. 26, 2008 in related pending U.S. Appl. No. 12/123,145.

Response to first Office Action dated Feb. 19, 2009 in related pending U.S. Appl. No. 12/123,145.

Restriction Requirement dated Mar. 20, 2009 in related pending U.S. Appl. No. 12/123,145.

Response to Restriction Requirement dated Apr. 17, 2009 in related pending U.S. Appl. No. 12/123,145.

Final Office Action dated May 28, 2009 in related pending U.S. Appl. No. 12/123,145.

Response to Final Office Action dated Jul. 28, 2009 in related pending U.S. Appl. No. 12/123,145.

Advisory Action dated Aug. 13, 2009 in related pending U.S. Appl. No. 12/123,145.

RCE dated Aug. 26, 2009 in related pending U.S. Appl. No. 12/123,145.

Article 19 Amendment filed Sep. 29, 2009 in connection with related International Application No. PCT/US2009/044464, Inventors Xindong Wu and Xingquan Zhu.

First Office Action After RCE dated Sep. 11, 2009 in connection with related U.S. Appl. No. 12/123,145.

Comments on Statement of Reason for Allowance dated May 19, 2010 in connection with related U.S. Appl. No. 12/123,145.

Response to First Office Action After RCE dated Jan. 11, 2010 in connection with related U.S. Appl. No. 12/123,145.

Notice of Allowance dated Mar. 16, 2010 in connection with related U.S. Appl. No. 12/123,145.

SYSTEMS FOR AND METHODS OF ASSESSING URINARY FLOW RATE VIA SOUND ANALYSIS

RELATED APPLICATION DATA

This application is a divisional of application U.S. application Ser. No. 11/530,314, filed Sep. 8, 2006, and titled "Systems For and Methods of Assessing Urinary Flow Rate Via Sound Analysis," which is incorporated by reference herein in its entirety. This application is also related to U.S. application Ser. No. 12/123,145, filed May 19, 2008, and titled "Systems For and Methods of Assessing Lower Urinary Tract Function Via Sound Analysis," now U.S. Pat. No. 7,758,519.

FIELD OF THE INVENTION

The present invention generally relates to the field of urinary flow analysis. In particular, the present invention is directed to systems for and methods of assessing urinary flow rate via sound analysis.

BACKGROUND

The measurement of a urinary flow rate is the simplest and widely used investigation in the assessment of voiding dysfunction. The urinary flow rate provides important and useful information about whether a problem exists in a patient's lower urinary tract. Additionally, the measurement of urinary flow rate may indicate the degree and possible etiology of an ongoing bladder pathology.

A uroflowmeter is a well-known device for measuring the rate of urine flow. Uroflowmeters that are commonly used today operate using one of three well-known methods: (1) a rotating disk method, (2) an electronic dipstick method, or (3) a gravimetric method. With the rotating disk method, voided fluid is directed onto a rotating disk and the amount landing on the disk produces a proportionate increase in its inertia. The power required to keep the disk rotating at a constant rate is measured, allowing calculation of the flow rate of fluid. In the electronic dipstick method, a dipstick is mounted in a collecting chamber and as urine accumulates the electrical capacitance of the dipstick changes, allowing calculation of the rate of fluid accumulation and hence the flow rate. With the gravimetric method, the weight of collected fluid or the hydrostatic pressure at the base of collecting cylinder is measured.

These uroflowmeters require that the user direct his/her urine stream into a device and, thus, today's uroflowmeters can be uncomfortable, messy, and difficult for the patient to use. Furthermore, the use of uroflowmeters in hospitals and doctor's offices poses a risk to medical personnel of contacting urine excrements. Additionally, collecting data using today's commercially available portable uroflowmeters is still unpractical, available only to a limited number of patients producing only limited number of measurements.

For these reasons, a need exists for improved systems for and methods of assessing urinary flow rate, in order to provide mechanisms for measuring urinary flow rate that are portable, convenient, easy to use in a non-stressful and risk-free environment and able to be used for mass examinations.

SUMMARY OF THE DISCLOSURE

The present disclosure, in one embodiment, is directed to a website operating on a server computing system. The website comprises a database operable on the server computing system for storing a file into a storage medium, the file including information representing the sounds of urination in a receptacle received from a telephone near, but not coupled to, the receptacle. The website includes a software routine executable on the server computer system for determining strength and duration of urination in a receptacle. The routine includes a first module that generates a plot of amplitude versus time of the sounds of the urination using the file, a second module that generates a set of numerical values that correspond to the strength and duration of the urination using the plot, and one or more web pages in which at least one of the following are displayed: the plot and the set of numerical values.

Another aspect of the disclosure is directed to a website for use in assessing urinary flow rates. The website comprises the features of receiving a signal from a telephone representing the sounds of urination into a preexisting volume of water in a receptacle, storing the signal in a storage medium as a file, determining strength and duration of urination from the file, and displaying the strength and duration results.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

The present disclosure is directed to a uroflow measurement system and method for determining strength and duration of urination in a manner more convenient than that typically available with known systems. In one embodiment, the sounds of urination in a receptacle such as a toilet are captured using a microphone or other device and are stored as an audio file. Sound analysis software is used to evaluate the information in the audio file and provide a representation of strength and duration of urination. In another embodiment, a telephone is used to capture the sounds of urination which are communication via a telephone system to uroflow management software and then to sound analysis software where analysis of urination sounds is performed. Either embodiment may be implemented via a website system, and alternatively, the audio file containing urination sound information may be send by email other means to the website system.

Figure 1:
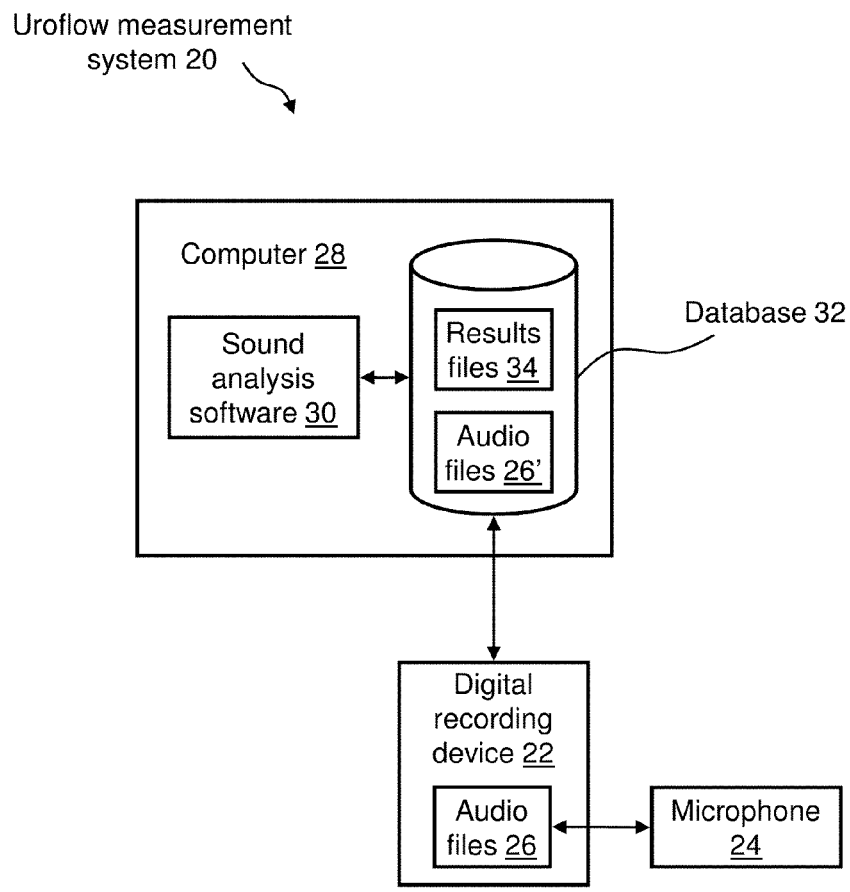
FIG. 1 illustrates a functional block diagram of a uroflow measurement system, in accordance with a first embodiment of the disclosure.

FIG. 1 illustrates a functional block diagram of a uroflow measurement system 20, in accordance with a first embodiment of the disclosure. Uroflow measurement system 20 provides mechanisms for measuring urinary flow rate by digitally capturing the sound of a patient urinating into a receptacle such as a toilet and, subsequently, performing an analysis thereof. Uroflow measurement system 20 includes a digital recording device 22 and a microphone 24. Additionally, a set of files such as audio files 26 are generated by, and stored upon digital recording device 22. Typically, although not necessarily, audio files 26 are digital files. Uroflow measurement system 20 further includes a computer 28 that comprises sound analysis software 30 and a database 32 upon which is stored a set of audio files 26' (typically but not necessarily digital files) and a set of results files 34.

Digital recording device 22 may be any commercially available portable sound recorder capable of capturing an audio input signal of microphone 24 and storing a representation thereof (i.e., any one of audio files 26) in any suitable audio file format, such as WAV format or MP3 format. Digital recording device 22 has a recording frequency in the range of, for example, but not limited to, 11025 to 44100 hertz (Hz). Additionally, digital recording device 22 may have an input/output port, such as, but not limited to, a universal serial bus (USB) port or firewire port, for transferring audio files 26 to an external computer, such as to computer 28. In other embodiments, digital recording device 22 may include a removable memory card (not shown) or other removable storage medium for transferring audio files 26 to an external computer. In yet other embodiments, digital recording device 22 may be integrated with computer 28. An example digital recording device 22 is the Sony ICB300 Digital Voice Recorder available from Sony Corporation, Tokyo, Japan. Microphone 24 may be a conventional microphone that is built into digital recording device 22. Alternatively, microphone 24 may be an external microphone that is in either wired or wireless communication with digital recording device 22. In the case of an external microphone, the use of a water resistant and/or floating microphone may be beneficial.

In the context of uroflow measurement system 20, the combination of digital recording device 22 and microphone 24 is one example of a mechanism for capturing the sound of a patient urinating into a receptacle such as a toilet, i.e., for capturing the sound of the urine stream. Each audio file 26 of digital recording device 22 is typically associated with a single urination event, although in some cases it may be desirable to use a single audio file 26 for multiple urination events.

Computer 28 may be any computer or computing resource, such as a handheld, laptop, desktop, or networked computer, that utilizes any suitable operating system, such as Microsoft Windows® 2000, Windows XP, Unix, Linux or Macintosh, that is capable of executing commercially available software applications or custom software applications, such as sound analysis software 30. Computer 28 typically includes a display for displaying the results of analysis of the sounds of urination, as described more below.

Database 32 may be created and maintained by any suitable database software, such as Oracle database software available from Oracle Corporation (Redwood Shores, Calif.), that stores relationships between patients and their associated audio files 26' and results files 34. Audio files 26' are audio files 26 of digital recording device 22 that have been transferred to database 32 of computer 28. Each audio file 26' will typically, although not necessarily, be associated with a particular patient. Results files 34 are data files that contain the results of the digital analysis of respective audio files 26'. The analysis is performed by sound analysis software 30, as described below.

Sound analysis software 30 is a software application that performs an analysis upon audio files 26', which, in the context of uroflow measurement system 20, are audio files may be a digital representation of the sound of a patient expelling urine into suitable receptacle, such as a toilet, i.e., a digital representation of the sound of a urine stream. In one example, the audio file may be a digital representation of the sound of urine striking the water in the toilet or the sides of the toilet where water is not maintained in the toilet bowl, or any other sound associated with urination. More specifically, sound analysis software 30 provides a visual/graphic analysis of a urination event and/or a set of numerical values that correspond to the strength and duration of the urination event. The present invention encompasses the use of any software for achieving the functions of software 30 described herein, as those of ordinary skill in the art will appreciate. The operations that are performed by sound analysis software 30 may include, but are not limited to, the following:

1. reading in the raw data of a selected audio file 26'. In doing so, the selected audio file 26' is converted into an array of amplitude readings at, for example, 8,000 data points per second;
2. generating a plot of audio signal amplitude vs. time. An example of such a raw data plot 40 appears in FIG. 2A. The audio signal amplitude represented in such a plot may be shown simply as the relative magnitude of the sound (i.e., no units), or may be shown as the fraction of the full possible amplitude of the sound signal, voltage, or any unit of sound volume;
3. generating a plot of smoothed data for the purpose of presenting an outline of the flow. For example, an envelope is calculated of, for example, the average positive amplitude per 100 data points. An example of such a smoothed data plot 42 appears in FIG. 2B;
4. referring to the smoothed data plot of the above-mentioned item 3, removing points that are less than a user-selected minimum percentage (e.g., 10%) of maximum amplitude. Subsequently, a plot of the largest continuous flow that has a strength that is greater than the minimum, i.e., a main flow plot, is generated. An example of this main flow plot 44 appears in FIG. 2C. Smaller lumps are discarded as spurts or drips. In doing so, a mechanism for comparing one audio file 26' to another with regard to "time to peak flow" is provided. The duration and time to peak flow starts at the beginning of the main flow as described above. Integration of other metrics of the main flow also provides a means of comparing one urination event to others;
5. by use of the main flow plot of the above-mentioned item 4, an analysis is performed in order to generate a set of numerical values that correspond to the strength and duration of urination. These values are used in order to compare numerically two or more urination events. An example of such a set of values is shown in an analysis window 46 that appears in FIG. 2D. Values include, but are not limited to, the following:

(a) MAXIMUM FLOW maximum measured in arbitrary units recorded in the course of a single urination event.

(b) TIME TO MAXIMUM FLOW—a measure of the time from the beginning of the main flow until the maximum amplitude is reached;

(c) VOIDING TIME—a measure of the time duration of the main flow;

(d) AVERAGE FLOW—the arithmetic mean of the main flow in arbitrary units. The mean is used for comparing two or more audio files 26'; and (e) SCORE—the integral of amplitude with time, which is then divided by a large number, e.g., one million, in order to generate a more ordinary number;

and 6. writing the above-mentioned plots and analysis to database 32 of computer 28.

Figure 2A:
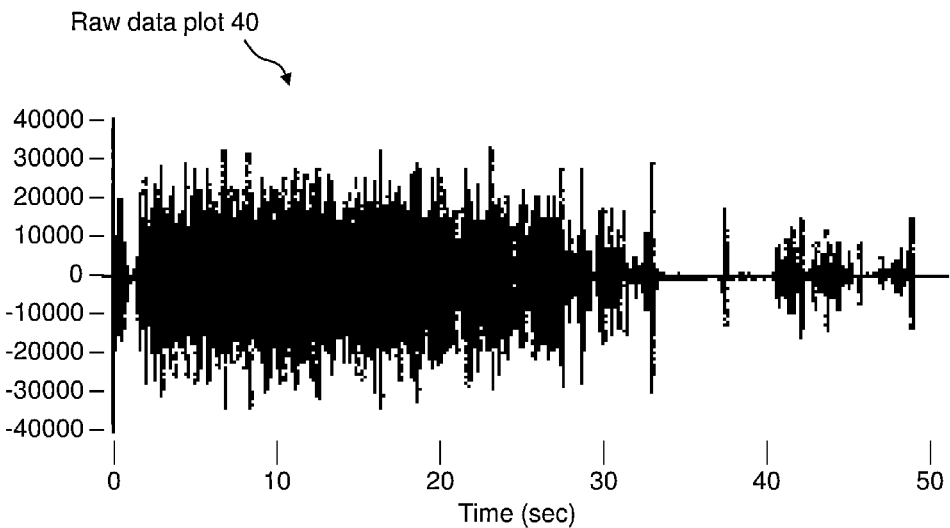
FIG. 2A illustrates a plot of the raw data of an audio file that is generated by use of the uroflow measurement system of FIG. 1.

As mentioned, FIG. 2A illustrates a raw data plot 40, which is the raw data from a selected one of audio files 26' that is generated by uroflow measurement system 20 of FIG. 1. More specifically, raw data plot 40 is a plot of audio signal amplitude vs. time of the selected audio file 26' in its entirety, which, again, is the digital representation of the sound of a stream of urine striking the water in a toilet or other receptacle during a urination event.

Figure 2B:
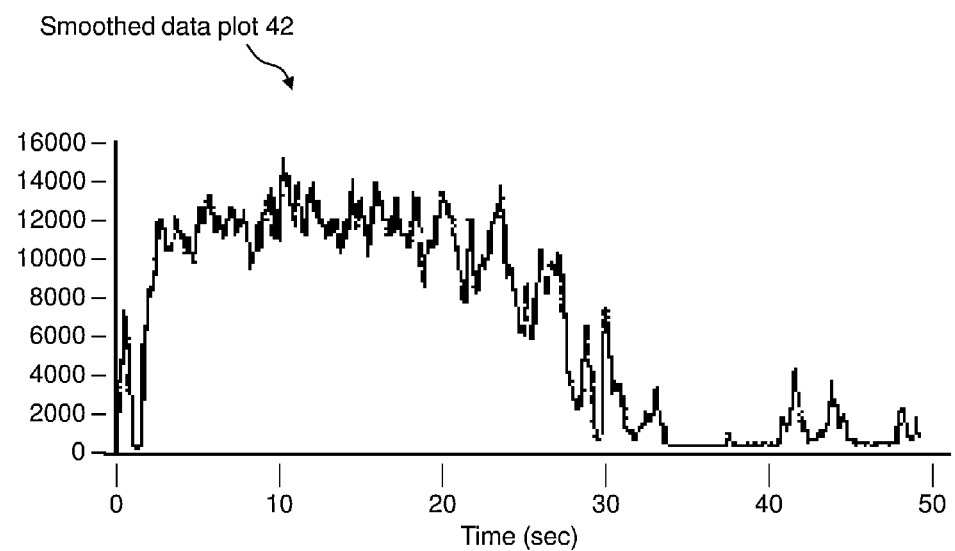
FIG. 2B illustrates a plot of the smoothed data of the raw data plot of FIG. 2A.

FIG. 2B illustrates smoothed data plot 42 of raw data plot 40 of FIG. 2A. More specifically, smoothed data plot 42 is an envelope that is a calculation of, for example, the average positive amplitude per 100 data points of raw data plot 40 of FIG. 2A. In doing so, smoothed data plot 42 shows an outline of the flow of the entire urination event. The present invention encompasses the use of any data smoothing algorithms that produce a result suitable for intended use, as known to those skilled in the art.

Figures 2C, 2D:
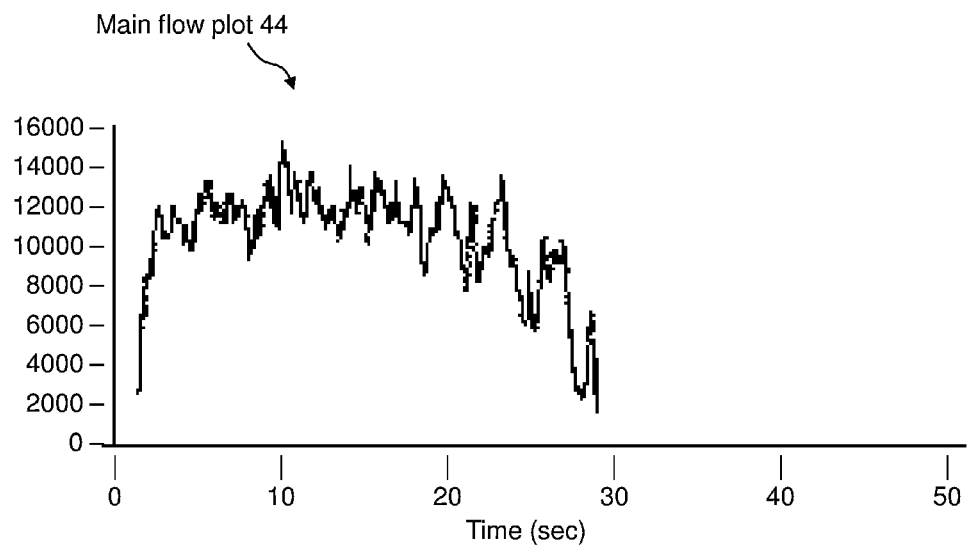
FIG. 2C illustrates a plot of a main flow, which is a subset of the smoothed data of FIG. 2B.
FIG. 2D illustrates an analysis window of the uroflow measurement system of FIG. 1.

FIG. 2C illustrates main flow plot 44, which is a selected portion of smoothed data plot 42 of FIG. 2B. More specifically, main flow plot 44 is a plot of the largest continuous flow that has a strength that is greater than the minimum. Smaller lumps that are present in smoothed data plot 42 that represent spurts or drips are discarded in arriving at main flow plot 44. For example, main flow plot 44 is the result of discarding the smaller leading and trailing lumps of smoothed data plot 42 of FIG. 2B.

FIG. 2D illustrates an analysis window 46 of uroflow measurement system 20 of FIG. 1, which is the result of sound analysis software 30 performing an analysis in order to generate a set of values that correspond to the strength and duration of urination. In the example of analysis window 46, values corresponding to MAXIMUM FLOW, TIME TO MAXIMUM FLOW, AVERAGE FLOW, VOIDING TIME, and SCORE are shown. These values are used in order to compare numerically two or more urination events. More details of the operation and use of uroflow measurement system 20 are in connection with FIG. 3.

Figure 3:
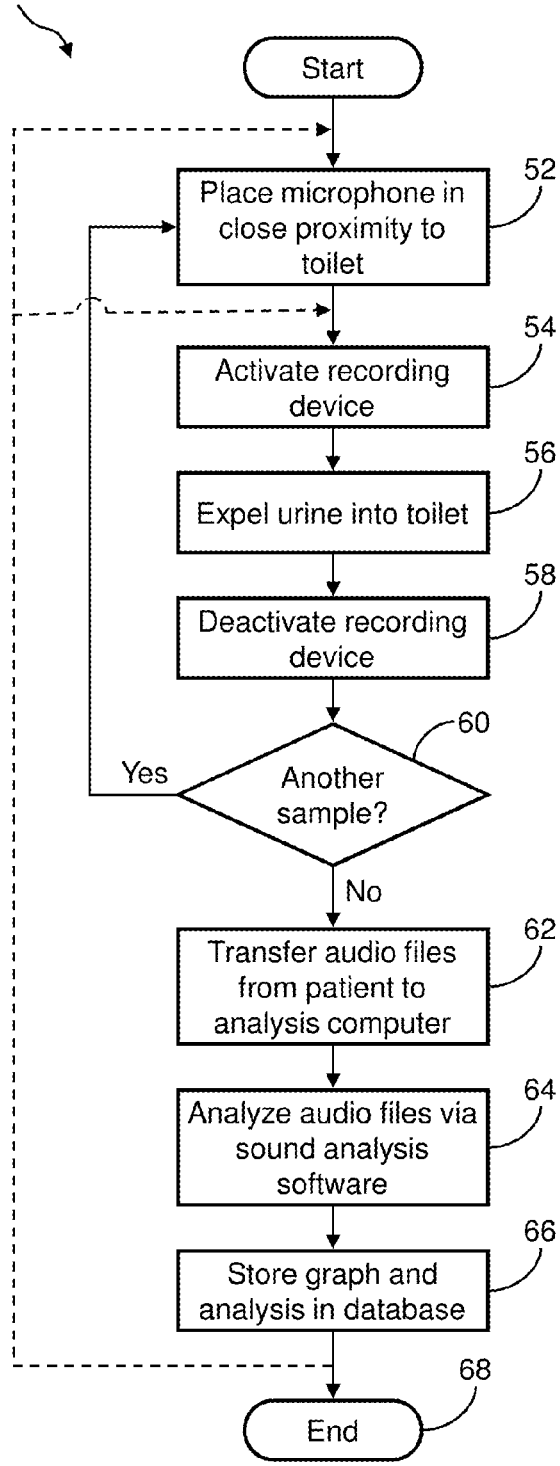
FIG. 3 illustrates a method of assessing urinary flow rate via sound analysis by use of the uroflow measurement system of FIG. 1, in accordance with a first embodiment of the disclosure.

FIG. 3 illustrates a method 50 of assessing urinary flow rate via sound analysis by use of uroflow measurement system 20 of FIG. 1, in accordance with one embodiment of the disclosure. At step 52, a user positions microphone 24 of digital recording device 22 in close proximity to the receptacle (not shown) into which he/she wishes to urinate. At step 54, the user activates digital recording device 22. At step 56, the user urinates into the receptacle. In doing so, digital recording device 22 captures the sound of the urine stream. At step 58, the user deactivates digital recording device 22 and removes digital recording device 22 and microphone 24 from the receptacle area. At decision step 60, the user decides whether he/she wishes to supply another sample, i.e., another audio file 26. If yes, method 50 returns to step 52. If no, method 50 proceeds to step 62.

At step 62, the user transfers one or more audio files 26 from digital recording device 22 to computer 28 via a USB connection, wireless connection, a memory card, or any other conventional means. In doing so, the one or more audio files 26 are stored upon database 32 of computer 28 as respective audio files 26' along with a tag for each that indicates the patient to which it is associated and/or any other pertinent information.

At step 64, sound analysis software 30 reads in each audio file 26' and performs an analysis thereon in order to determine the strength and duration of each urination event, such as described above in connection with FIGS. 1, 2A, 2B, 2C, and 2D. In doing so, a set of graphs, such as raw data plot 40 of FIG. 2A, smoothed data plot 42 of FIG. 2B, and main flow plot 44 of FIG. 2C, along with a set of numerical values, such as shown in analysis window 46 of FIG. 2D, are generated for each urination event. Again, example values that are displayed in analysis window 46 may include, but are not limited to, MAXIMUM FLOW, TIME TO MAXIMUM FLOW, AVERAGE FLOW, VOIDING TIME, and SCORE, as described above in connection with FIGS. 1, 2A, 2B, 2C, and 2D.

At step 66, the graphs and values of step 64 are stored in database 32 as a corresponding results file 34 for each urination event. This information may be used for the assessment of urine flow rate and duration as well as for comparing one urination event to another for the purpose of establishing urination patterns and history. Method 50 may end at step 68 or may return to, for example, either step 52 or step 54.

Figure 4:
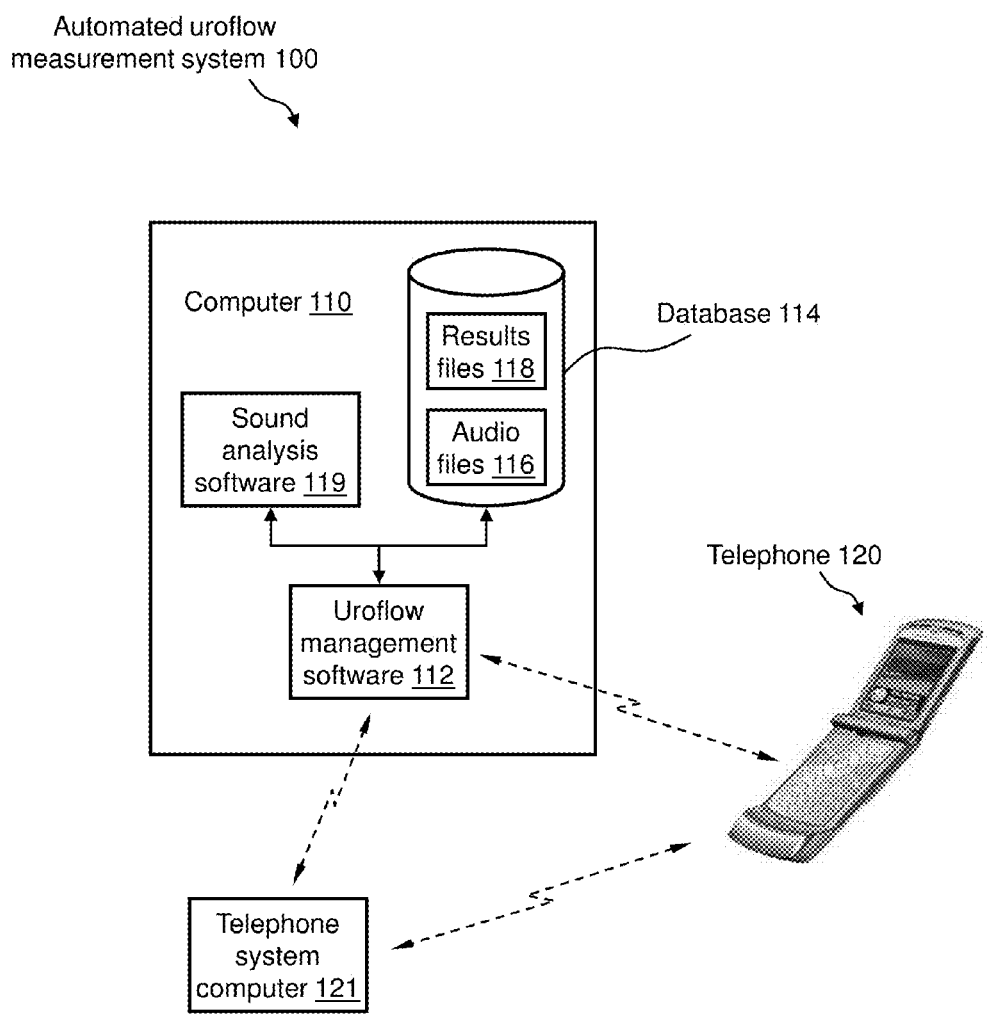
FIG. 4 illustrates a functional block diagram of an automated uroflow measurement system, in accordance with a second embodiment of the disclosure.

FIG. 4 illustrates a functional block diagram of an automated uroflow measurement system 100, in accordance with a second embodiment of the disclosure. Automated uroflow measurement system 100 provides mechanisms for measuring urinary flow rate by capturing over the telephone the sound of a patient urinating into a receptacle and, subsequently, performing an analysis thereof in an automated fashion. Automated uroflow measurement system 100 includes a computer 110 that comprises uroflow management software 112 and a database 114 upon which is stored a set of audio files 116 and a set of results files 118. Also residing on computer 110 is sound analysis software 119 that may be the same as, or similar to, software 30 that is described above in connection with FIGS. 1, 2A, 2B, 2C, 2D, and 3. Automated uroflow measurement system 100 further includes a telephone 120 that is electrically connected to telephone system computer 121 by use of wired or cellular infrastructure, as is well known, or telephone 120 may be electrically connected to computer 110 by use of wired or cellular infrastructure, as is well known.

Telephone system computer 121 is, e.g., representative of an application server that is associated with any private or commercially available cellular, landline or other telephone service provider. Example telephone service providers include, but are not limited to, Verizon Wireless (Bedminster, N.J.), Sprint Nextel (Reston, Va.), Time Warner Cable (Stamford, Conn.), and Verizon (New York, N.Y.). Telephone system computer 121 may capture, store and send telephone recordings (e.g., voice mails). Uroflow management software 112 is the software application that manages the overall functions that are related to measuring urinary flow rate. More specifically, uroflow management software 112 obtains its sound data from telephone system computer 121 (e.g., via e-mail attachment, ftp or other means of transferring sound data or files) or from real-time stream of sound from telephone 120, makes the analysis thereof by use of sound analysis software 119, stores the results in the database 114, and manages all of the foregoing. The results may be communicated back to the user by email, ftp or other means of transferring digital files, or made available on a web site. Telephone 120 may be any commercially available (or specifically constructed) telephone or cellular telephone.

Database 114 may be created and maintained by any suitable database management software, such as the above-mentioned Oracle database software, that stores relationships between patients and their associated audio files 116 and results files 118. Audio files 116 are audio files of the sound of corresponding respective urination events that are received at telephone system computer 121 via telephone 120. Audio files 116 may have any suitable audio file format, such as WAV format or MP3 format. Each audio file 116 is typically associated with a particular patient and may carry a timestamp. Results files 118 are data files that contain the results of the digital analysis of respective audio files 116. This analysis is performed by sound analysis software 119, for example, as described above in connection with software 30 and FIGS. 1, 2A, 2B, 2C, 2D, and 3.

Figure 5:
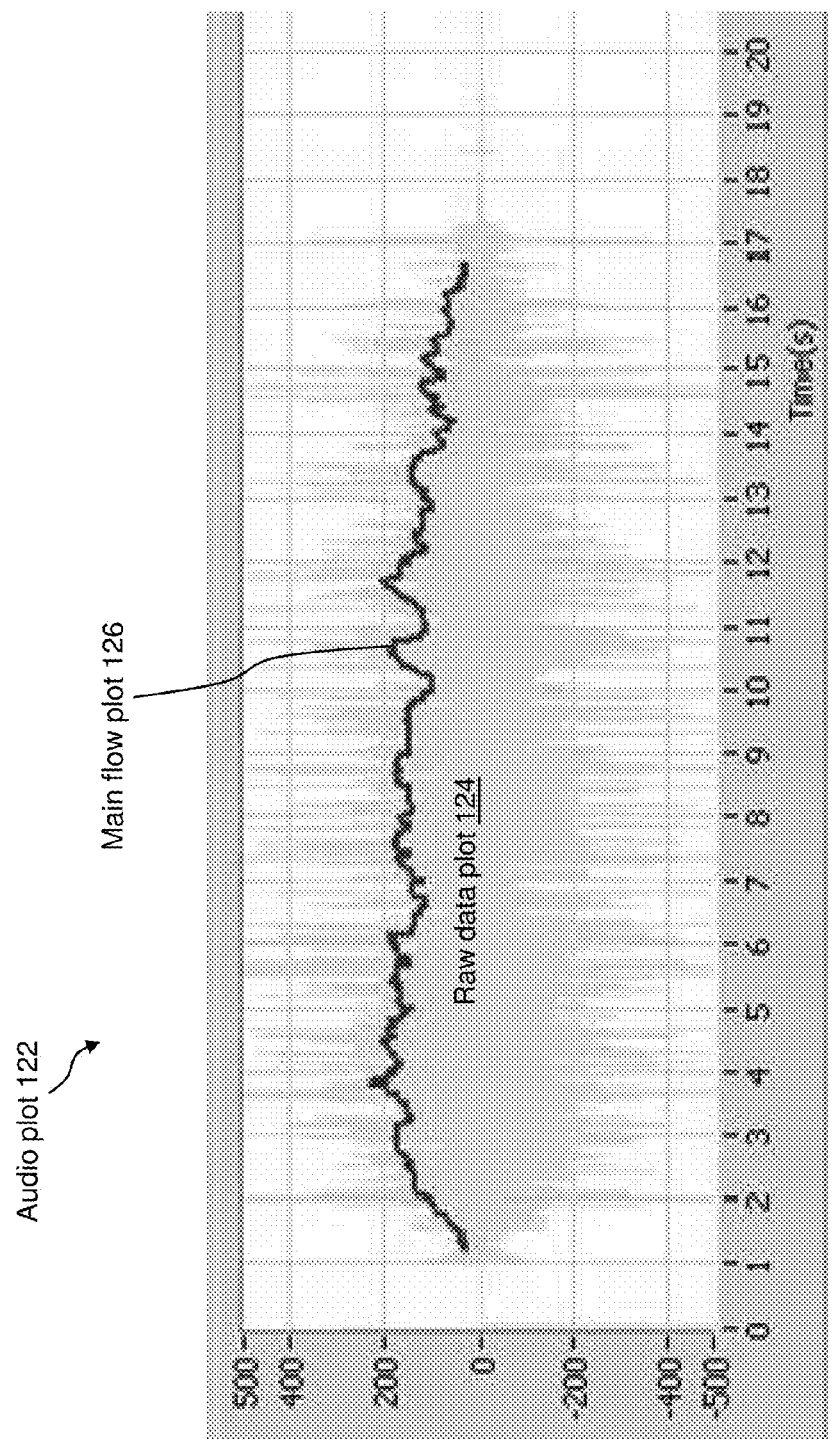
FIG. 5 illustrates a plot showing both the raw data and the main flow as derived from an audio file that is generated by use of the automated uroflow measurement system of FIG. 4.

FIG. 5 illustrates a combined audio plot 122 derived from an audio file 116 that may be generated by use of automated uroflow measurement system 100 of FIG. 4. Audio plot 122 is a combination of a raw data plot 124 upon which is overlaid a main flow plot 126. More specifically, raw data plot 124 is a plot of audio signal amplitude vs. time of a selected audio file 116 in its entirety, which is the digital representation of the sound of a stream of during a urination event, such as described above with respect to raw data plot 40 of FIG. 2A. Main flow plot 126 is a selected portion of raw data plot 124. More specifically, main flow plot 126 is a plot of the largest continuous flow having a strength greater than the minimum. Smaller lumps that are present in raw data plot 124 that represent spurts or drips are discarded generally in the manner described with respect to main flow plot 44 of FIG. 2C. More details of the operation and use of automated uroflow measurement system 100 are presented below in connection with FIG. 6.

Figure 6:
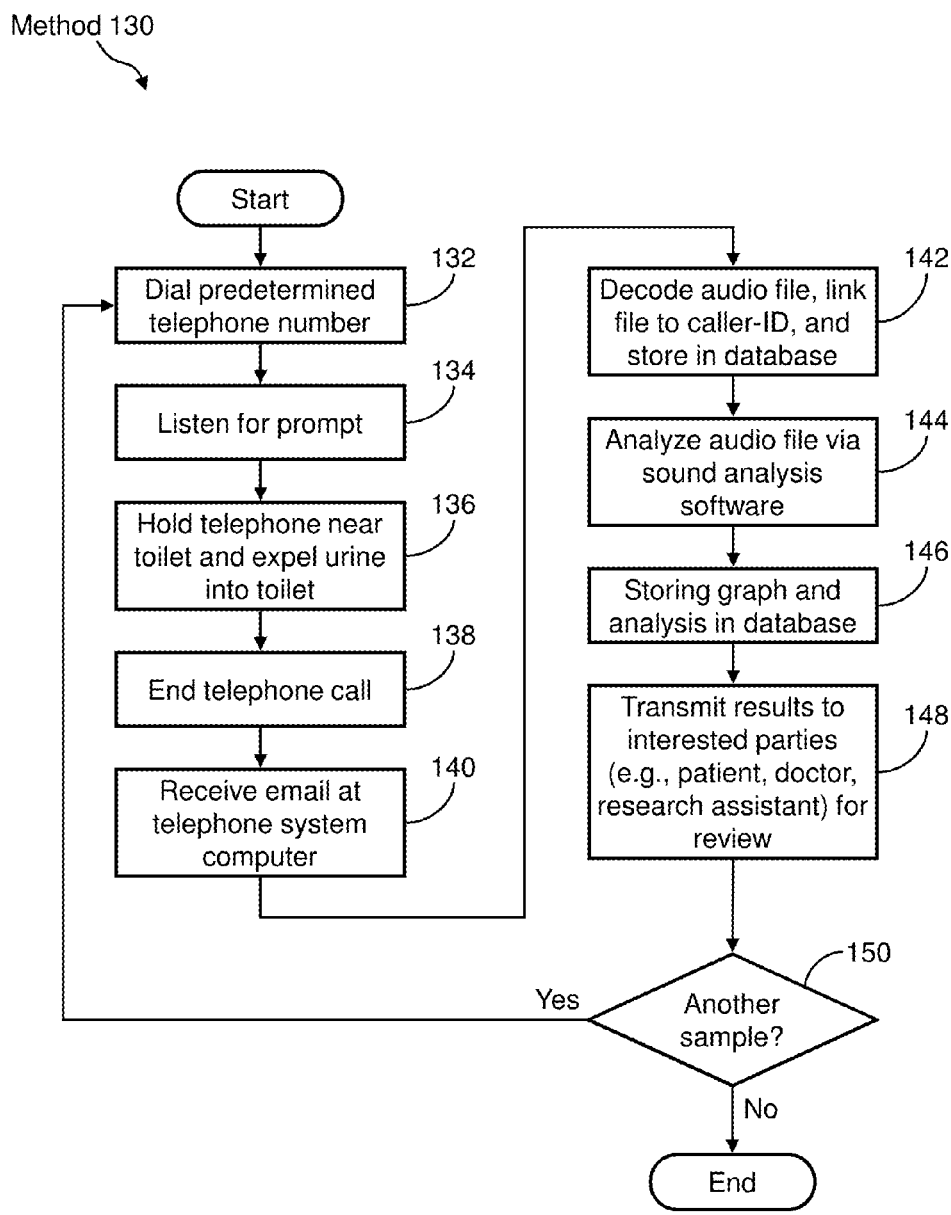
FIG. 6 illustrates a method of automatically assessing urinary flow rate via sound analysis by use of the automated uroflow measurement system of FIG. 4, in accordance with a second embodiment of the disclosure.

FIG. 6 illustrates a method 130 of assessing automatically urinary flow rate via sound analysis by use of automated uroflow measurement system 100 of FIG. 4, in accordance with a second embodiment of the disclosure. At step 132, a user who wishes to have his/her urine flow rate analyzed dials a predetermined telephone number by use of his/her telephone 120. In doing so, the user is connected to computer 110 of automated uroflow measurement system 100 via his/her telephone 120. The user may also be connected to a voicemail system which stores the sounds of urination for later processing by the telephone system computer. The phone number may be, for example, a toll free telephone number that is established by the administrator of automated uroflow measurement system 100 and provided to patients by their respective physicians.

At step 134, having dialed the predetermined telephone number at step 132, the user listens on his/her telephone 120 for a prompt to begin urinating into his/her toilet or other receptacle. The prompt may be a beep, prerecorded voice, or any audible prompt. At step 136, a user positions his/her telephone 120 in close proximity to the receptacle (not shown) into which he/she wishes to urinate. Subsequently, the user urinates into the receptacle. In doing so, the sound is transmitted via telephone 120 to telephone system computer 121. At step 138, upon completion of the urination event, the telephone call is ended by user hanging up his/her telephone 120.

At step 140, upon completion of the telephone call, an email that has an audio file 116 attached thereto is received automatically at computer 110. Audio file 116 is the digital representation of the sound of the urine stream during micturition. At step 142, uroflow management software 112 of computer 110 decodes the given audio file 116 that is received via email in order to link the given audio file 116 to the caller-ID. Subsequently, the given audio file 116 is stored in database 114 along with its unique identification information and a timestamp.

At step 144, sound analysis software 30 reads in the given audio file 116 and performs an analysis thereon in order to determine the strength and duration of the urination event, such as described with reference to FIGS. 1 through 5. In doing so, a set of graphs, such shown in audio plot 122 of FIG. 5 (e.g., raw data plot 124 and main flow plot 126), along with a set of values, such as shown in analysis window 46 of FIG. 2D, are generated for the urination event. Example values include, but are not limited to, MAXIMUM FLOW, TIME TO MAXIMUM FLOW, AVERAGE FLOW, VOIDING TIME, and SCORE, as described with respect to FIGS. 1, 2A, 2B, 2C, and 2D.

At step 146, the graphs and values of step 144 are stored in database 114 as a corresponding results file 118 for the given urination event. This information may be used for the assessment of urine flow rate and duration as well as for comparing one urination event to another for the purpose of establishing urination patterns and history.

At step 148, the graphs and values of step 146, which are the results of the analysis that is performed in step 144, are transmitted to the patient's doctors and/or the patient for review. The transmission may occur, for example, via email or voicemail under the control of uroflow management software 112 of computer 110. Also a web site link may be provided into which the patient may log in and access his/her results. At decision step 150, the user decides whether he/she wishes to supply another sample, i.e., another audio file 116. If yes, method 130 returns to step 132. If no, method 130 may end.

Figure 7:
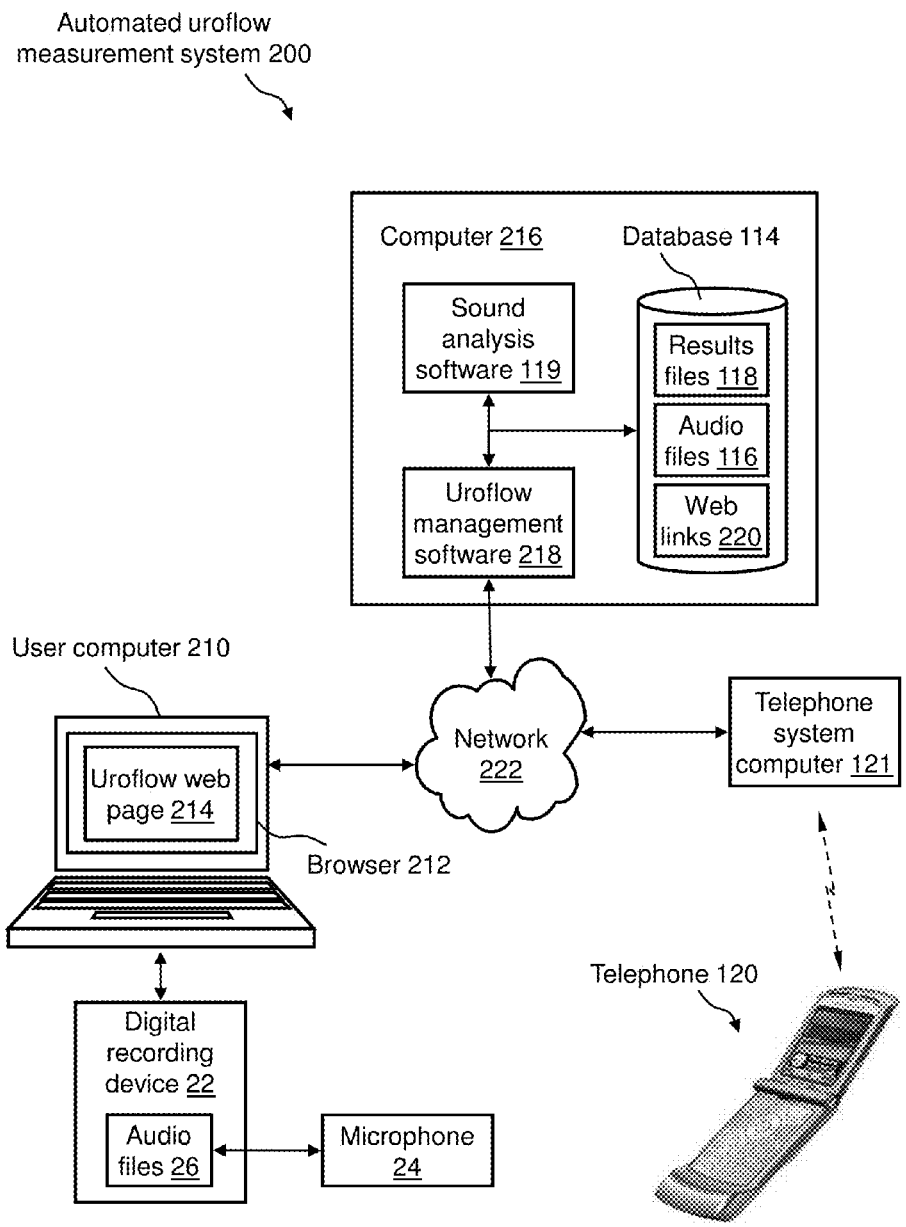
FIG. 7 illustrates a functional block diagram of an automated uroflow measurement system, in accordance with a third embodiment of the disclosure.

FIG. 7 illustrates a functional block diagram of an automated uroflow measurement system 200, in accordance with a third embodiment of the disclosure. Automated uroflow measurement system 200 includes a user computer 210 that is in communication with digital recording device 22 that contains audio files 26 and that is connected to microphone 24. Digital recording device 22, microphone 24, and audio files 26 as described above in connection to uroflow measurement system 20 of FIG. 1. Additionally, user computer 210 includes a browser 212 by which a uroflow website 214 is displayed to the user of user computer 210. Automated uroflow measurement system 200 further includes a computer 216 that includes database 114 and sound analysis software 119, which are described above with connection to automated uroflow measurement system 100 of FIG. 4, and uroflow management software 218. Database 114 includes audio files 116 and results files 118, which are described above with connection to automated uroflow measurement system 100 of FIG. 4, and a collection of web links 220. Automated uroflow measurement system 200 further includes telephone 120 and telephone system computer 121, which are likewise described above in connection with automated uroflow measurement system 100 of FIG. 4. Furthermore, a communication link is provided between user computer 210, computer 216, and telephone system computer 121 by use of a network 222, which may be any suitable wired or wireless network, such as a local area network (LAN), a wide area network (WAN), or the Internet.

Computer 210 and computer 216 may be any standard computer or computing resource, such as a handheld, laptop, desktop, or networked computer, that utilizes any suitable operating system, such as Microsoft Windows® 2000, Windows XP, Unix, Linux, or Macintosh, that is capable of executing commercially available software applications or custom software applications, such as, in the case of computer 216, sound analysis software 119.

Browser 212 of computer 210 may be any suitable Internet browser application, such as, but not limited to, Windows® Internet Explorer or Netscape® Navigator. Uroflow website 214 is a website that is provided to a user accessing uroflow management software 218 of computer 216 via network 222. More specifically, a user accesses, via his/her user computer 210, web links 220 of database 114 that are associated with uroflow website 214. Uroflow website 214 serves as a graphical user interface (GUI) by which the user may access the web-based uroflow application of computer 216, which is formed by the combination of database 114, sound analysis software 119, and uroflow management software 218. In particular, under the control of uroflow management software 218 of computer 216, a user may login to the web-based uroflow application. The function of uroflow management software 218 is substantially identical to that of management software 112 of automated uroflow measurement system 100 of FIG. 4, except for the additional function of managing the web-based uroflow application that allows a patient, doctor, or other interested party to login and view the results of the sound analysis of one or more urination events that is performed by sound analysis software 119. In doing so, the strength and duration of one or more urination events, such as described with connection to FIGS. 1 through 6, are displayed to the user via uroflow website 214 in the display of user computer 210. More specifically, a set of graphs, along with a set of numerical values, such as, but not limited to, MAXIMUM FLOW, TIME TO MAXIMUM FLOW, AVERAGE FLOW, VOIDING TIME and SCORE, are presented to the user via uroflow website 214. More details of an example uroflow website 214 are provided with reference to FIGS. 8A and 8B.

Figure 8A:
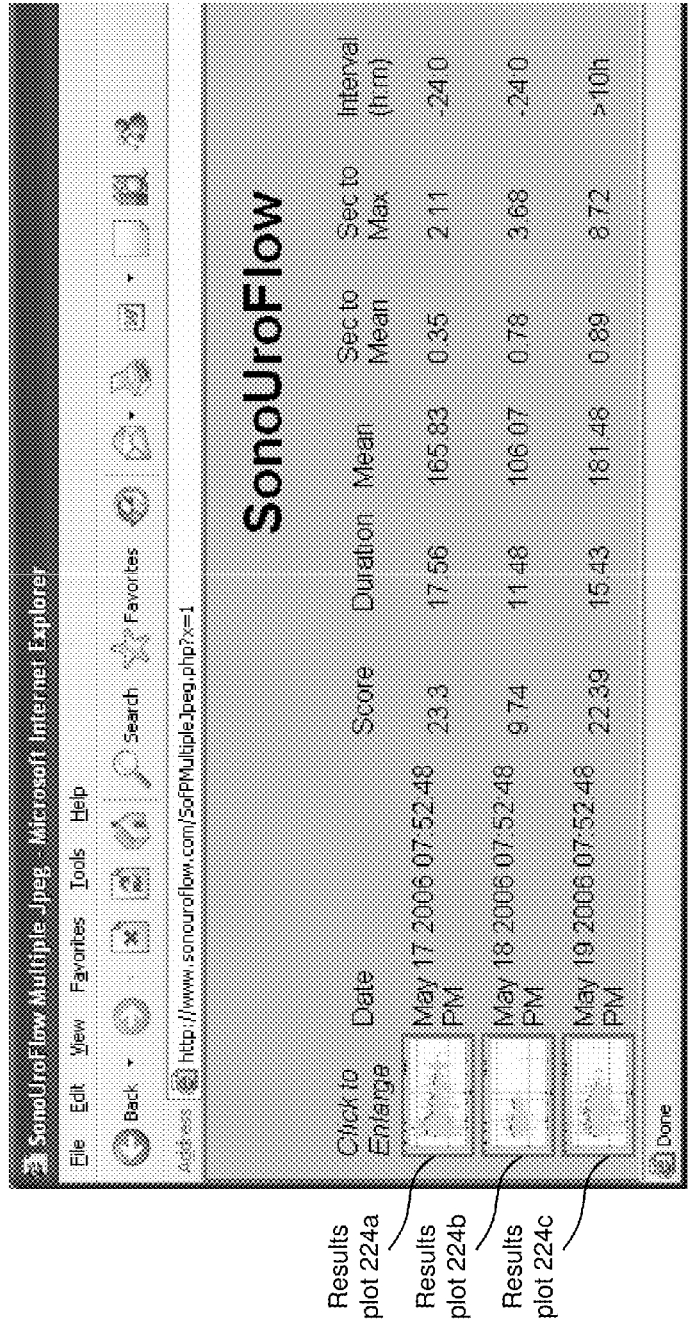
FIG. 8A illustrates a uroflow web page that is provided by use of the automated uroflow measurement system of FIG. 7.

FIG. 8A illustrates one instance of uroflow website 214 that is provided by use of automated uroflow measurement 200 system of FIG. 7. In the example shown in FIG. 8A, the analysis of three urination events from the same individual is displayed to the user in graphical fashion via uroflow website 214, which is displayed within browser 212 of his/her user computer 210. Displayed as a numerical value for each of the three urination events is a MAXIMUM FLOW, TIME TO MAXIMUM FLOW, AVERAGE FLOW, VOIDING TIME and SCORE. Also displayed for each of the three urination events is a "thumbnail" of a results plot 224, e.g., a thumbnail of a results plot 224a, 224b and 224c. In one embodiment of uroflow website 214, by clicking on the thumbnail of a given results plot 224, the selected results plot is enlarged, as shown in more detail in FIG. 8B.

Figure 8B:
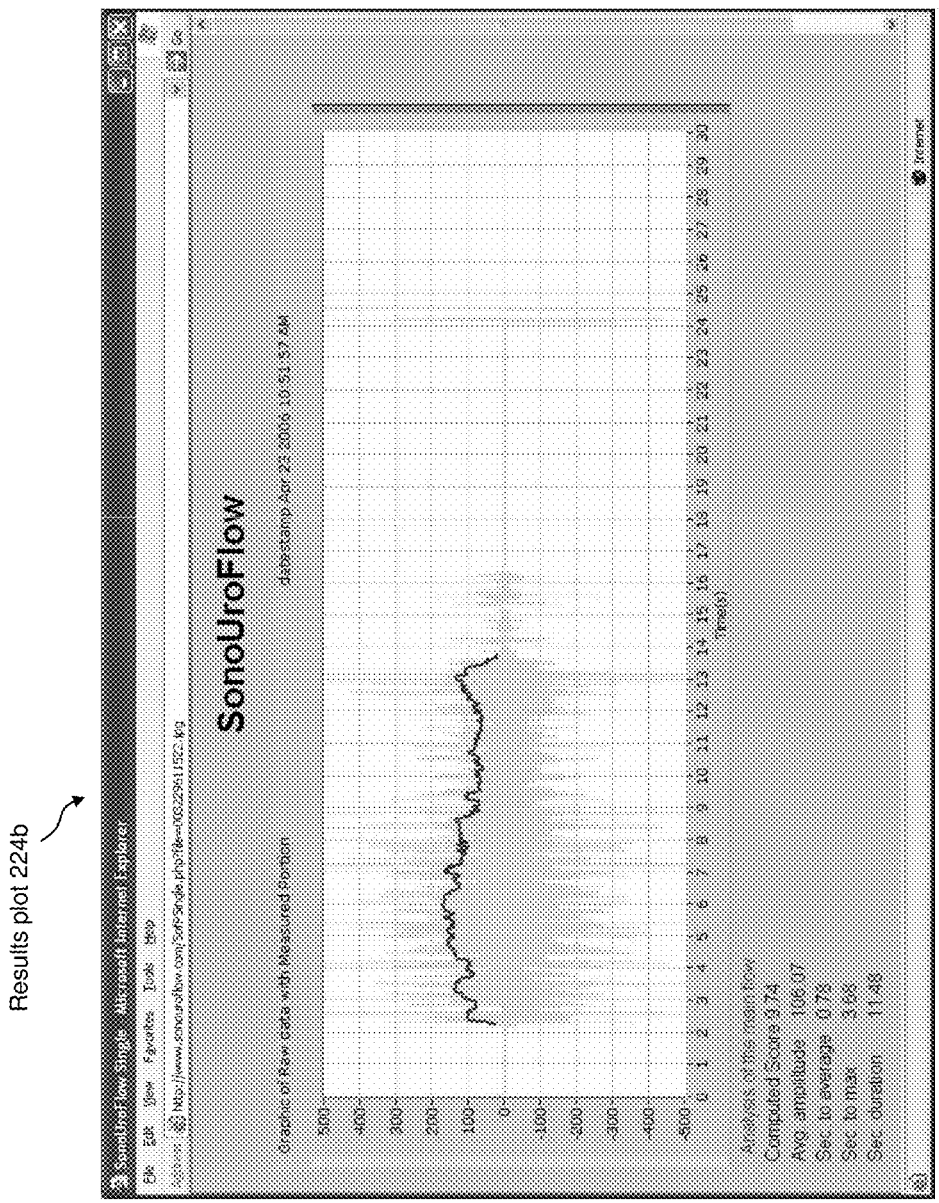
FIG. 8B illustrates an example results plot that is provided by use of the automated uroflow measurement system of FIG. 7.

FIG. 8B illustrates an example results plot 224 that is provided by use of uroflow website 214 of automated uroflow measurement system 200 of FIG. 7. By way of example, FIG. 8B shows an enlarged view of results plot 224b of uroflow website 214 of FIG. 8A. More specifically, results plot 224b of uroflow website 214 is a graphical representation of, for example, the combination of raw data plot 40 of FIG. 2A, smoothed data plot 42 of FIG. 2B, main flow plot 44 of FIG. 2C, and analysis window 46 of FIG. 2D. The enlarged graphical representation of results plot 224b is displayed to the user within browser 212 of his/her user computer 210.

Referring again to FIGS. 7, 8A, and 8B, the operation of automated uroflow measurement system 200 is as follows. An audio file of a urination event is captured either by use of digital recording device 22 and microphone 24 or by use of telephone 120. In the case of digital recording device 22 and microphone 24, the urination event is stored as an audio file 26. The associated audio file 26 is then transferred to user computer 210 from which a user may email (by any conventional email application) the associated audio file 26 to computer 216 via network 222. Alternatively, uroflow website 214 may make provision to transfer the associated audio file 26 to computer 216. The user's audio file 26 is saved in database 114 as, for example, an audio file 116. However, in the case of a patient using telephone 120, the sound of a urination event is transferred to computer 216 by use of telephone system computer 121, as described in connection to automated uroflow measurement system 100 of FIG. 4, and network 222. Again, the user's audio file is saved in database 114 as, for example, an audio file 116. In either case, stored along with audio file 116 may be an identification mechanism (e.g., a telephone number) for linking the file to its source (i.e., to a specific patient) and a timestamp. Having saved one or more audio files 116 to database 114 of computer 216, sound analysis software 119 executes in order to generate MAXIMUM FLOW, TIME TO MAXIMUM FLOW, AVERAGE FLOW, VOIDING TIME and SCORE and the plots of the urination event, such as results plots 224a, 224b, and 224c, as shown in uroflow website 214 of FIG. 8A. Subsequently, a doctor, patient, or other authorized interested party may access the web-based uroflow application of computer 216 by use of uroflow website 214, in order to view, in graphical fashion, the results of one or more urination events.

In summary, a uroflow measurement system made in accordance with the present disclosure, such as uroflow measurement system 20 of FIG. 1, automated uroflow measurement system 100 of FIG. 4, and automated uroflow measurement system 200 of FIG. 7, provide mechanisms for assessing urinary flow rate via sound analysis. Uroflow measurement system 20, automated uroflow measurement system 100, and automated uroflow measurement system 200 are designed for easy use in a patient's home, which eliminates the negative effects and stressfulness of the test environment and, provides more reliable test results. Uroflow measurement system 20, automated uroflow measurement system 100, and automated uroflow measurement system 200 may be used for initial screening and follow-up with treatment of persons in all age groups, including pediatric and adolescent patients. Additionally, the use of either of uroflow measurement system 20, automated uroflow measurement system 100, or automated uroflow measurement system 200 allows the micturition process to be studied and allows for better understanding of the development of micturition as well as to be able to determine several types of abnormal voiding habits during early childhood and puberty that later lead to specific voiding dysfunctions. Additionally, the use of either of these systems provides patients an easy and quick way to assess their lower urinary tract function and treatment effects, which gives clinicians more accurate information and helps to monitor the dynamics of the disease and the progress of therapy management overall. Furthermore, the use of a uroflow measurement system of the present disclosure may allow mass preventive examinations, more precisely select patient population seeking medical help and diminish the contact of medical personnel with urine excrements.

In addition, the use of a uroflow measurement system of the present disclosure, such as either of uroflow measurement system 20, automated uroflow measurement system 100, or automated uroflow measurement system 200, that provide urine flow measurement based on sound transduction may be used in medical research in order to test effects of new drugs that are intended to be employed in the treatment of bladder dysfunctions.

While the present invention may be satisfactorily performed using a toilet to receive the urination, it is not so limited. If desired, urination may occur in other receptacles. Generally speaking, suitable alternative receptacles will tend to reflect rather than absorb the sounds of urination so as to permit the sounds of urination to be readily transmitted and captured by digital recording device 22 or other suitable device.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A plurality of programs stored on a storage medium on at least one server computing system, the plurality of programs executable by said at least one server computing system to operate a website, the plurality of programs comprising:
   a. a database program operable on the at least one server computing system for storing a file into the storage medium, the file including information representing the sounds of urination into an air-liquid interface received from a telephone near, but not coupled to, the interface;
   b. a software program executable on the at least one server computer system for determining strength and duration of urination at the air-liquid interface, said program including:
      i. a first module that generates a plot of amplitude versus time of the sounds of the urination using said file; and
      ii. a second module that generates a set of numerical values that correspond to the strength and duration of the urination using said plot; and
   c. a software program executable on the at least one server computer system for generating one or more web pages in which at least one of the following are displayed: said plot and said set of numerical values.

2. A plurality of programs according to claim 1, including a user interface for permitting a user to transmit information representing the sounds of urination at the air-liquid interface to the at least one server computer system.

3. A plurality of programs according to claim 1, wherein said set of numerical values includes at least one of the following: maximum flow, time to maximum flow, voiding time, average flow and score.

4. A plurality of programs according to claim 1, wherein said database program is further operable to store images representing said plot.

5. A plurality of programs according to claim 1, further including a user interface for permitting limited access to files stored in the database program.

6. A program for use in assessing urination, the program stored on a storage medium on a server computing system, the program executable by said server computing system to operate a website to perform the steps of:
   a. receiving a signal from a telephone representing a sound of urination into an air-liquid interface;
   b. storing the signal in the storage medium as a file;
   c. assessing the strength and duration of urination from the file; and
   d. converting the results of said assessing strength and duration of urination into a form displayable on the website.

7. A program according to claim 6, wherein said determining step includes generating a plot of amplitude versus time of the sounds of the urination using the file.

8. A program according to claim 7, wherein said determining step includes generating a set of numerical values that correspond to the strength and duration of the urination using the plot.

* * * * *